US007540432B2

(12) United States Patent
Majerowski et al.

(10) Patent No.: US 7,540,432 B2
(45) Date of Patent: Jun. 2, 2009

(54) PASSIVE DISPENSING DEVICE

(75) Inventors: Amelia H. Majerowski, Kenosha, WI (US); Martin S. Payne, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 245 days.

(21) Appl. No.: 11/442,802

(22) Filed: May 30, 2006

(65) Prior Publication Data

US 2007/0290064 A1    Dec. 20, 2007

(51) Int. Cl.
*A24F 25/00* (2006.01)
*A61L 9/04* (2006.01)

(52) U.S. Cl. .......................... 239/51.5; 239/34; 239/44; 239/47; 239/53; 239/57; 239/59

(58) Field of Classification Search .................. 239/34, 239/44, 47, 51.5, 53, 57, 58, 59
See application file for complete search history.

(56) References Cited

U.S. PATENT DOCUMENTS

| | | | |
|---|---|---|---|
| 2,383,960 | A | 9/1945 | Dupuy |
| 2,614,820 | A | 10/1952 | Doydjieff |
| 3,330,481 | A | 7/1967 | Dearling |
| 3,976,246 | A | 8/1976 | Hauri et al. |
| 4,219,145 | A | 8/1980 | Jaeschke et al. |
| 4,306,679 | A | 12/1981 | Dusek et al. |
| 4,327,056 | A | 4/1982 | Gaiser |
| 4,339,079 | A | 7/1982 | Sato et al. |
| 4,523,870 | A | 6/1985 | Spector |
| 4,537,351 | A | 8/1985 | Wilson |
| 4,621,768 | A | 11/1986 | Lhoste et al. |
| 4,707,338 | A | 11/1987 | Spector |
| 4,739,928 | A | * 4/1988 | O'Neil ........................ 239/45 |
| 4,745,705 | A | 5/1988 | Yamamoto et al. |

(Continued)

FOREIGN PATENT DOCUMENTS

DE    25 45 598    10/1975

(Continued)

OTHER PUBLICATIONS

PCT/US2007/012355 International Search Report and Written Opinion dated May 15, 2008.

*Primary Examiner*—Len Tran
*Assistant Examiner*—Ryan Reis

(57) ABSTRACT

A passive dispensing device for a liquid active material includes an upper housing portion for receiving a container for holding and dispensing a liquid active material, wherein the upper housing portion includes an interior cavity and wherein the container includes a wick extending from inside the container to an area outside the container. The device further includes a lower housing portion that extends downwardly from the upper housing portion, wherein the lower housing portion defines a recess between the upper and lower housing portions and includes first and second legs that extend downwardly from the upper housing portion and outwardly from the recess. The device has an operative position in which the first and second legs are disposed on a support surface, the container is retained in the recess with the wick extending upwardly into the interior cavity, and the container is spaced above the support surface and disposed between the first and second legs to allow convective air flow past the recess and the container through the device to dispense the active material from the upper housing.

20 Claims, 6 Drawing Sheets

U.S. PATENT DOCUMENTS

| | | |
|---|---|---|
| 4,857,240 A | 8/1989 | Kearnes et al. |
| 4,866,580 A | 9/1989 | Blackerby |
| 4,878,615 A | 11/1989 | Losi |
| 4,913,349 A | 4/1990 | Locko |
| 4,913,350 A | 4/1990 | Purzycki |
| 4,917,301 A | 4/1990 | Munteanu |
| 4,928,881 A | 5/1990 | Barlics et al. |
| 4,931,224 A | 6/1990 | Holzer, Sr. |
| 4,938,419 A | 7/1990 | Weick |
| D309,943 S | 8/1990 | Jones et al. |
| 4,968,487 A | 11/1990 | Yamamoto et al. |
| RE33,864 E | 3/1992 | Steiner et al. |
| 5,095,647 A | 3/1992 | Zobele et al. |
| 5,114,625 A | 5/1992 | Gibson |
| 5,126,078 A | 6/1992 | Steiner et al. |
| 5,133,042 A | 7/1992 | Pelonis |
| 5,217,696 A | 6/1993 | Woverton et al. |
| 5,223,182 A | 6/1993 | Steiner et al. |
| 5,242,111 A | 9/1993 | Nakoneczny et al. |
| 5,250,265 A | 10/1993 | Kawaguchi et al. |
| 5,277,877 A | 1/1994 | Jeffrey et al. |
| 5,342,584 A | 8/1994 | Fritz et al. |
| 5,370,829 A | 12/1994 | Kunze |
| 5,376,338 A | 12/1994 | Zlotnik |
| 5,437,410 A | 8/1995 | Babasade |
| D365,390 S * | 12/1995 | King .................... D23/367 |
| D365,391 S | 12/1995 | King |
| 5,647,053 A | 7/1997 | Schroeder et al. |
| 5,651,942 A | 7/1997 | Christensen |
| 5,662,835 A | 9/1997 | Collingswood |
| D385,024 S | 10/1997 | Roberts |
| D386,564 S | 11/1997 | Mycroft |
| D386,974 S | 12/1997 | Wefler |
| 5,695,692 A | 12/1997 | Kennedy |
| D393,063 S | 3/1998 | Wefler |
| 5,851,442 A | 12/1998 | Spector |
| 5,891,400 A | 4/1999 | Ansari et al. |
| 5,909,845 A | 6/1999 | Greatbatch et al. |
| 5,919,423 A | 7/1999 | Requejo et al. |
| 5,970,643 A | 10/1999 | Gawel, Jr. |
| 5,980,064 A | 11/1999 | Metroyanis |
| 6,017,139 A | 1/2000 | Lederer |
| 6,104,867 A * | 8/2000 | Stathakis et al. ............ 392/403 |
| 6,106,786 A | 8/2000 | Akahoshi |
| 6,196,706 B1 | 3/2001 | Cutts |
| 6,241,161 B1 | 6/2001 | Corbett |
| 6,354,710 B1 | 3/2002 | Nacouzi |
| 6,361,752 B1 | 3/2002 | Demarest et al. |
| 6,371,450 B1 | 4/2002 | Davis et al. |
| D456,886 S | 5/2002 | Hart et al. |
| D458,359 S | 6/2002 | Blanchette |
| D460,544 S | 7/2002 | Garcia |
| 6,454,425 B1 | 9/2002 | Lin |
| 6,484,438 B2 | 11/2002 | Matsunaga et al. |
| 6,514,467 B1 | 2/2003 | Bulsink et al. |
| 6,555,068 B2 | 4/2003 | Smith |
| 6,567,613 B2 | 5/2003 | Rymer |
| 6,610,254 B1 | 8/2003 | Furner et al. |
| 6,616,308 B2 | 9/2003 | Jensen et al. |
| 6,619,560 B1 | 9/2003 | Chun |
| D480,309 S | 10/2003 | Choke-arpornchai et al. |
| D487,144 S | 2/2004 | Choke-arpornchai et al. |
| D488,546 S | 4/2004 | Harbutt et al. |
| 6,846,462 B2 | 1/2005 | Stanley, III |
| 6,854,717 B2 | 2/2005 | Millan |
| 6,859,615 B2 | 2/2005 | Yip et al. |
| 6,862,403 B2 | 3/2005 | Pedrotti et al. |
| 6,938,883 B2 | 9/2005 | Adams et al. |
| D516,690 S | 3/2006 | Harbutt et al. |
| 7,014,818 B2 | 3/2006 | Rymer |
| 7,025,283 B2 | 4/2006 | Torres |
| 7,032,831 B2 * | 4/2006 | Duston et al. .................. 239/44 |
| 7,140,553 B2 | 11/2006 | Zobele |
| 7,159,792 B2 | 1/2007 | Wheatley et al. |
| 7,160,515 B2 | 1/2007 | Murdell et al. |
| 7,185,827 B2 | 3/2007 | Quintard et al. |
| 2002/0080601 A1 | 6/2002 | Meltzer |
| 2002/0093834 A1 | 7/2002 | Yu et al. |
| 2002/0136542 A1 | 9/2002 | He et al. |
| 2002/0136886 A1 | 9/2002 | He et al. |
| 2003/0007887 A1 | 1/2003 | Roumpos et al. |
| 2003/0053305 A1 | 3/2003 | Lin |
| 2003/0180194 A1* | 9/2003 | Massimo .................... 422/124 |
| 2004/0141315 A1 | 7/2004 | Sherburne |
| 2004/0182949 A1 | 9/2004 | Duston et al. |
| 2004/0246711 A1 | 12/2004 | Brenchley et al. |
| 2004/0265189 A1 | 12/2004 | Schwatrz |
| 2004/0265196 A1 | 12/2004 | Varanasi et al. |
| 2005/0002834 A1 | 1/2005 | Gohil |
| 2005/0178345 A1* | 8/2005 | Crapser ..................... 122/366 |
| 2005/0226788 A1 | 10/2005 | Hrybyk et al. |
| 2005/0265189 A1 | 12/2005 | Tai |
| 2006/0016904 A1 | 1/2006 | Caserta et al. |
| 2006/0022064 A1 | 2/2006 | Triplett et al. |
| 2006/0202050 A1 | 9/2006 | Caserta et al. |
| 2006/0231213 A1* | 10/2006 | Matsuda et al. ............ 159/27.3 |
| 2006/0249593 A1 | 11/2006 | Brown et al. |
| 2006/0260183 A1 | 11/2006 | Hockaday |
| 2006/0283888 A1 | 12/2006 | Kinscherf et al. |
| 2006/0291826 A1* | 12/2006 | Hafer et al. ................. 392/395 |
| 2007/0057086 A1 | 3/2007 | Van Kippersluis |
| 2007/0065332 A1 | 3/2007 | Stiros et al. |

FOREIGN PATENT DOCUMENTS

| | | |
|---|---|---|
| DE | 32 23 780 | 3/1983 |
| EP | 0200493 A2 | 4/1986 |
| EP | 1486365 A2 | 12/2004 |
| EP | 1 516 634 | 3/2005 |
| EP | 1595552 A1 | 11/2005 |
| EP | 1627648 A1 | 2/2006 |

* cited by examiner

PASSIVE DISPENSING DEVICE

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to passive dispensing devices, and more particularly, to passive dispensing devices with improved air flow.

2. Description of the Background of the Invention

A multitude of liquid active material emitting devices or diffusers exist in the marketplace. Many of such devices are passive devices that require only ambient air flow around the device to disperse a liquid active material. Other devices have a cord and plug extending from the device, a plug extending directly from the device, or batteries, to power elements of the device. Such powered devices may include a heater, a fan, a piezoelectric actuator, or other means by which the liquid active material is dispensed from the device.

One powered active material emitting device includes a housing and a fan disposed within the housing for dispensing a liquid active material disposed. The liquid active material is disposed within a reservoir and a wick is in contact with the liquid active material and extends out of the reservoir. The wick is disposed adjacent the fan when the reservoir is inserted into the device and vents are disposed in the housing opposite the fan to disperse the liquid active material into the surroundings.

A passive active material emitting device has been developed for automobiles where it is difficult to power an electronic device. The passive automobile device includes a front portion attached to a back portion by a hinge, wherein the front and back portions include vents therein. The front portion may be pivoted about the hinge to insert a container therein, wherein the container includes a wick extending therefrom and in contact with a liquid active material disposed in the container. The front portion is thereafter moved to a closed position to enclose the wick and a top portion of the container between the front and back portions, wherein liquid active material is dispersed into the atmosphere via the vents in the front and rear portions. The back portion includes a clip extending therefrom, wherein the clip is inserted into and retained in position by a slat of a vent.

Other passive active material emitting devices include a reservoir with a liquid active material disposed therein and a porous membrane disposed on a bottom surface of the device. The device further includes legs that space the porous membrane from a support surface. The porous membrane allows the liquid active material to move through the membrane to a bottom, exposed surface of the membrane to be evaporated by natural air flow that travels between the bottom surface and the legs of the device.

Although many active material emitting devices are adapted to be positioned on a supporting surface, some devices are adapted to be suspended or attached to a vertical surface. One such device includes a housing having an aperture in a bottom portion of the housing. A disc-shaped cartridge containing one or more solid active materials therein is disposed within the housing. The housing is preferably attached by adhesive tape or the like to a movable member, such as a door. Movement of the door causes a pulse of air to flow into the housing through the aperture, thereby producing a concentrated dose of fragrance to be emitted from the solid active material that is disposed adjacent the aperture.

SUMMARY OF THE INVENTION

According to one aspect of the present invention, a passive dispensing device for a liquid active material includes an upper housing portion for receiving a container for holding and dispensing a liquid active material, wherein the upper housing portion includes an interior cavity and wherein the container includes a wick extending from inside the container to an area outside the container. The device further includes a lower housing portion that extends downwardly from the upper housing portion, wherein the lower housing portion defines a recess between the upper and lower housing portions and includes first and second legs that extend downwardly from the upper housing portion and outwardly from the recess. The device has an operative position in which the first and second legs are disposed on a support surface, the container is retained in the recess with the wick extending upwardly into the interior cavity, and the container is spaced above the support surface and disposed between the first and second legs to allow convective air flow past the recess and the container through the device to dispense the active material from the upper housing.

According to another aspect of the present invention, a passive dispensing device for a liquid active material includes a housing having first and second body portions defining upper and lower housing portions. First and second clips extend inwardly from the upper housing portion, wherein each of the clips includes two outer engaging portions and an inner indentation. The dispensing device further includes a container for holding the liquid active material, wherein the container includes a wick extending from inside the container to an area outside the container, a recess disposed in a first wall of the container, and a downwardly facing ledge disposed in a second wall of the container. The container is disposed within the device such that the outer engaging portions of the first clip engage walls defining the recess, the outer engaging portions of the second clip engage the ledge, and the indentations for passageways between the container walls and the clips.

According to still another aspect of the present invention, a passive dispensing device for a liquid active material includes a container for holding the liquid active material, wherein the container includes a wick that extends from inside the container to an area outside the container. The dispensing device further includes an upper housing portion for dispensing the volatile material, wherein the upper housing portion includes an interior cavity. Still further, the dispensing device includes a lower housing portion extending downwardly from the upper housing portion, wherein the lower housing portion defines a recess between the upper and lower housing portions and the lower housing portion further includes first and second legs extending downwardly from the upper housing portion and outwardly from the recess. The dispensing device has an operative position in which the container is retained in the recess with the wick extending upwardly into the interior cavity, a bottom surface of the container is disposed above bottom surfaces of the legs, and the container is disposed between the first and second legs such that gaps are formed between the container and the legs to allow convective air flow past the container through the device.

Other aspects and advantages of the present invention will become apparent upon consideration of the following detailed description and the attached drawings, in which like elements are assigned like reference numerals.

DETAILED DESCRIPTION OF THE INVENTION

FIGS. 1-8 illustrate a passive dispensing device 20 for an active material disposed within a container 22. The active material is liquid in form and may be, for example, an insecticide, an insect repellent, an insect attractant, a disinfectant, a mold or mildew inhibitor, a fragrance, a disinfectant, an air purifier, an aromatherapy scent, an antiseptic, an odor eliminator, a positive fragrancing active material, an air-freshener, a deodorizer, or the like, and combinations thereof.

Figure 8:
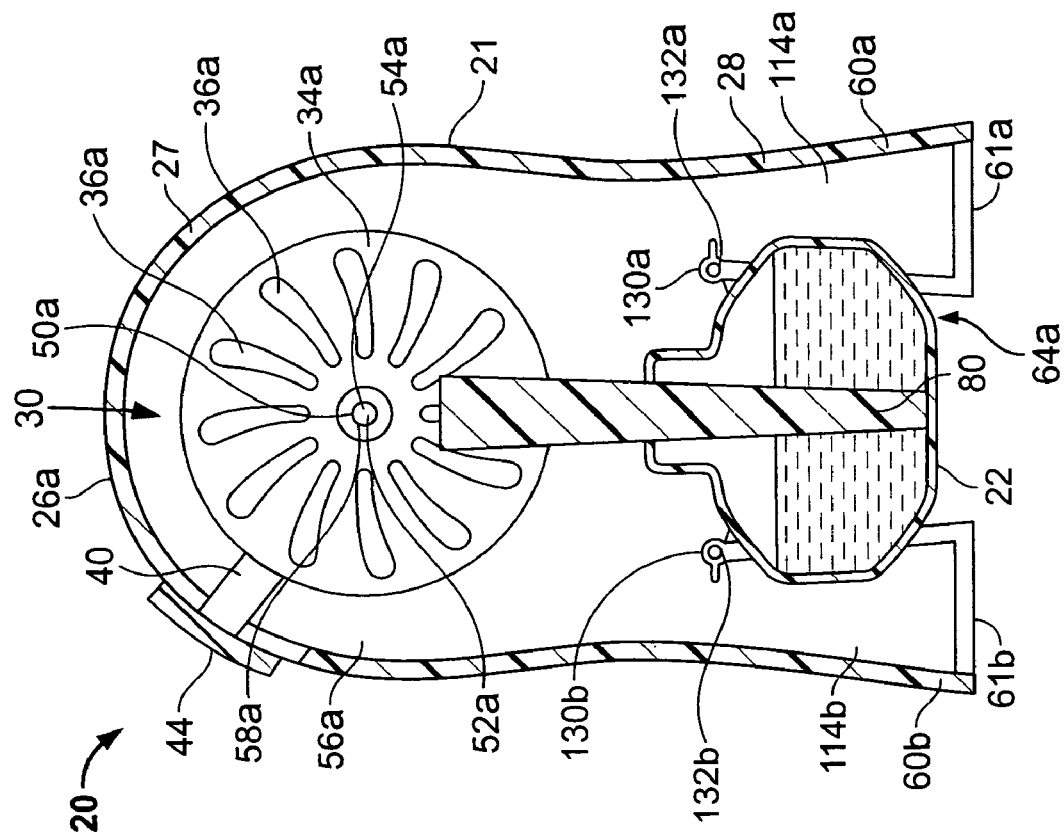
FIG. 8 is a cross-sectional view taken generally along the lines 8-8 of FIG. 3, wherein the dispensing device includes a container inserted therein.
Figure 7:
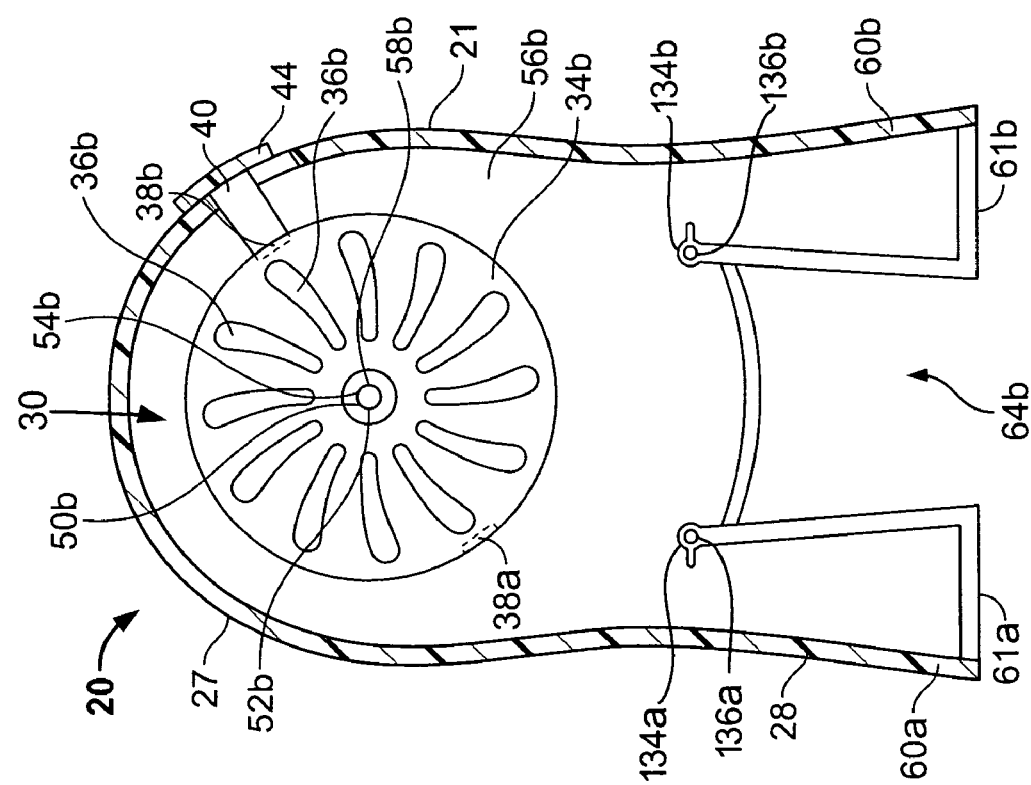
FIG. 7 is a cross-sectional view taken generally along the lines 7-7 of FIG. 3.

The dispensing device 20 includes a housing 21 having first and second body portions 26a, 26b defining upper and lower housing portions 27, 28. The first and second body portions 26a, 26b of the upper housing portion 27 define an interior cavity 30. The first and second body portions 26a, 26b of the upper housing portion 27 further include first and second sets of vents 32a, 32b, respectively, wherein first and second circular louvers 34a, 34b, are centered within the first and second sets of vents 32a, 32b. Referring to FIGS. 7 and 8, the first and second louvers 34a, 34b each include a plurality of louver vents 36a, 36b, respectively therein, and the louvers 34a, 34b are connected to one another by two rails 38a, 38b. An arm 40 extends outwardly from the rail 38a through a slot 42 formed between the first and second body portions 26a, 26b, wherein the arm 40 terminates in a knob 44.

The first and second louvers 34a, 34b include first and second apertures 50a, 50b through center points 52a, 52b thereof. First and second circular posts 54a, 54b extend from inner surfaces 56a, 56b, respectively, of the first and second body portions 26a, 26b into the interior cavity 30. The first and second posts 54a, 54b engage walls 58a, 58b defining the apertures 50a, 50b in the louvers 34a, 34b. Movement of the knob 44 in a first direction along the slot 42 rotates the louvers 34a, 34b about the center points 52a, 52b to an open position in which the first and second sets of vents 32a, 32b are aligned with the respective louver vents 36a, 36b. When the knob is moved in a second opposite direction to a closed position, the first and second sets of vents 32a, 32b are no longer aligned with the respective louver vents 36a, 36b.

Figure 1:
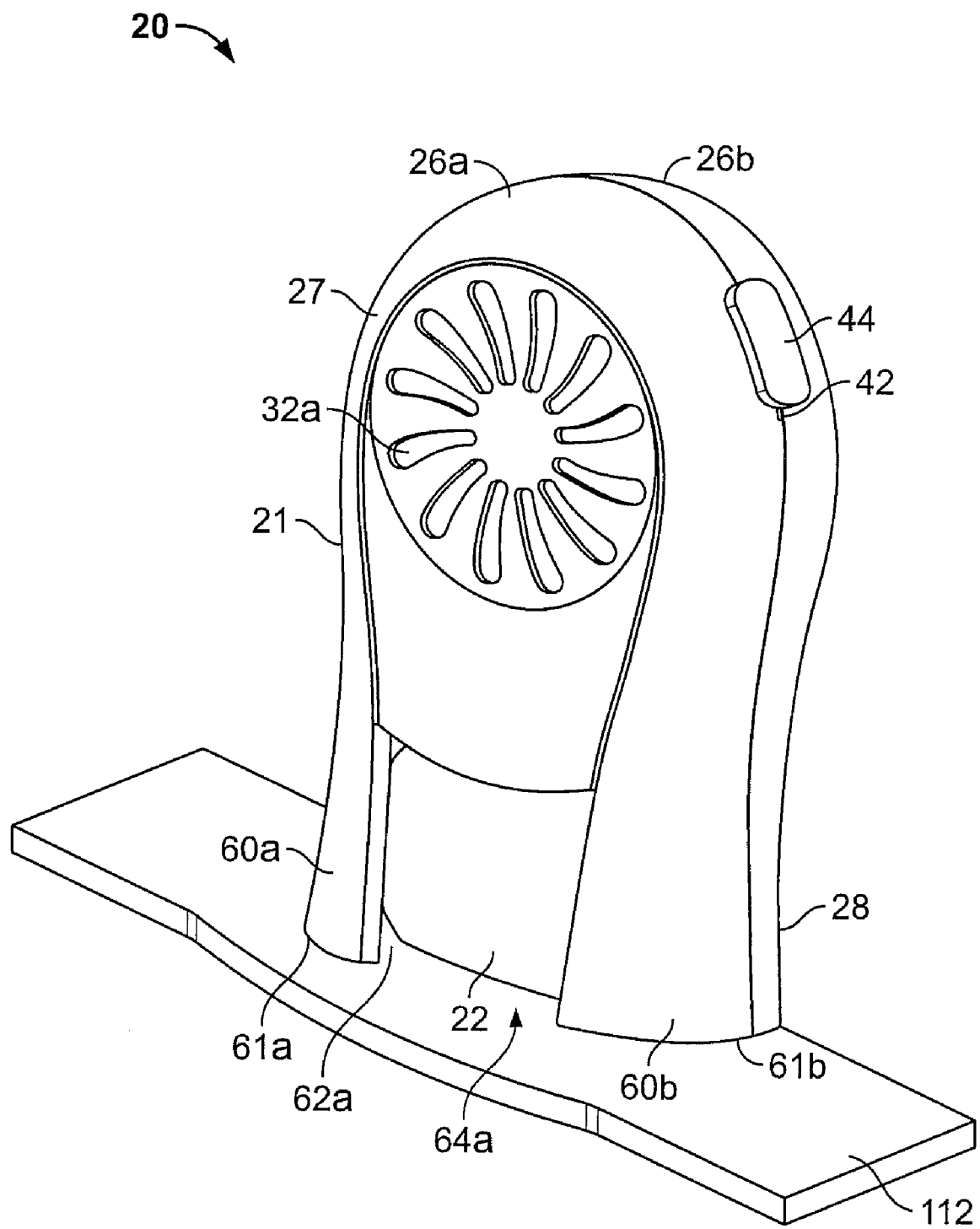
FIG. 1 is a front isometric view of a passive dispensing device disposed on a support surface and having a container inserted therein.
Figure 3:
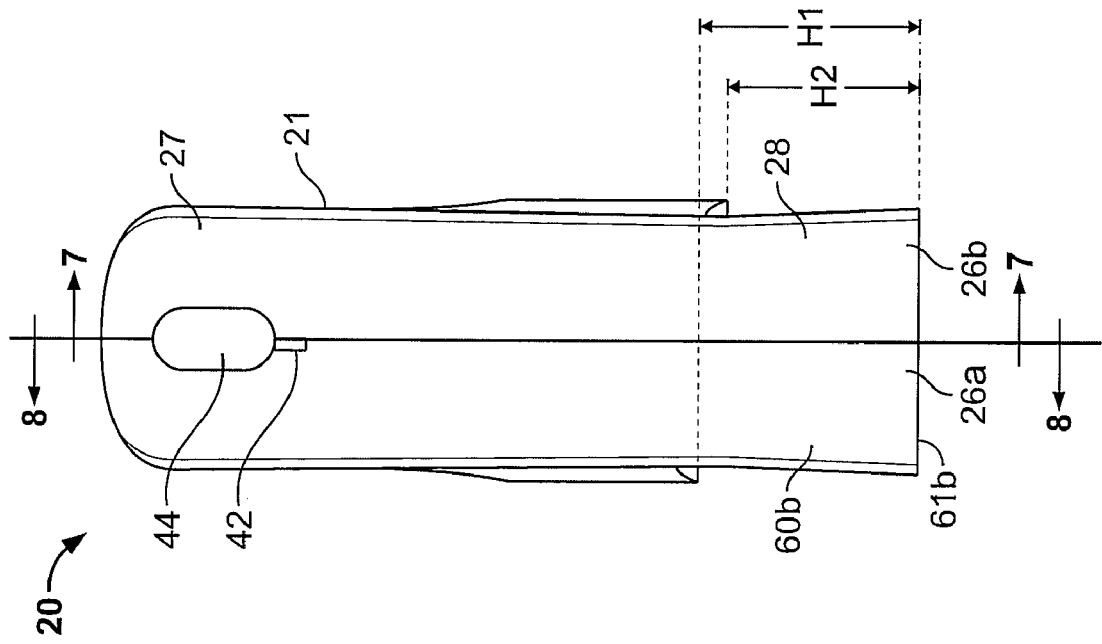
FIG. 3 is an elevational view of a second side of the dispensing device of FIG. 1.
Figure 2:
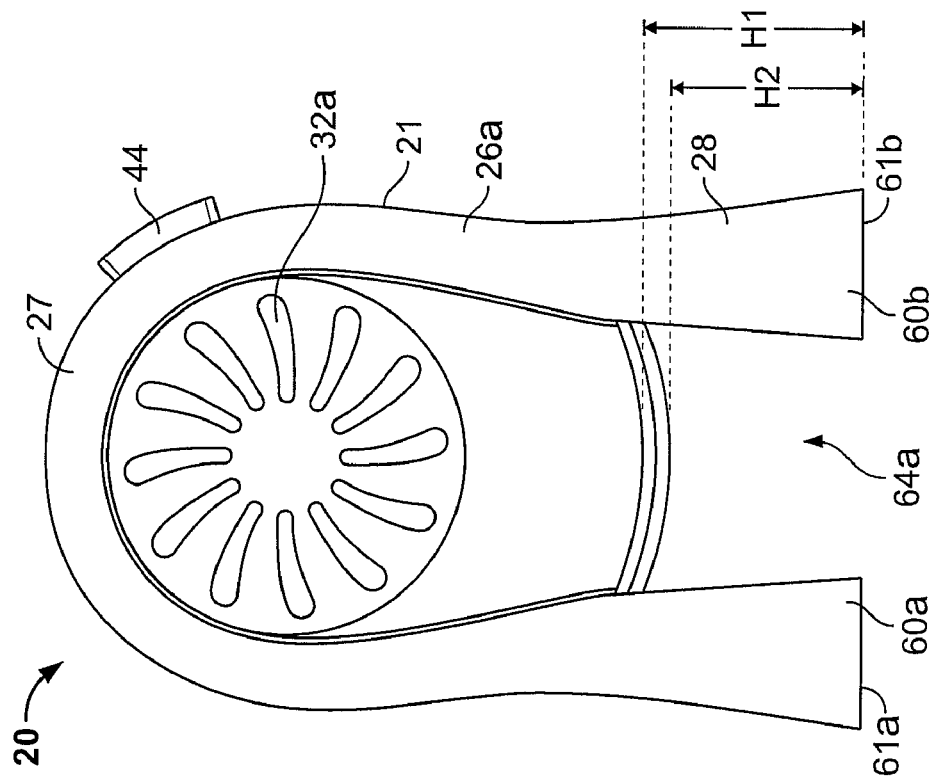
FIG. 2 is an elevational view of a first side of the dispensing device of FIG. 1.
Figure 4:
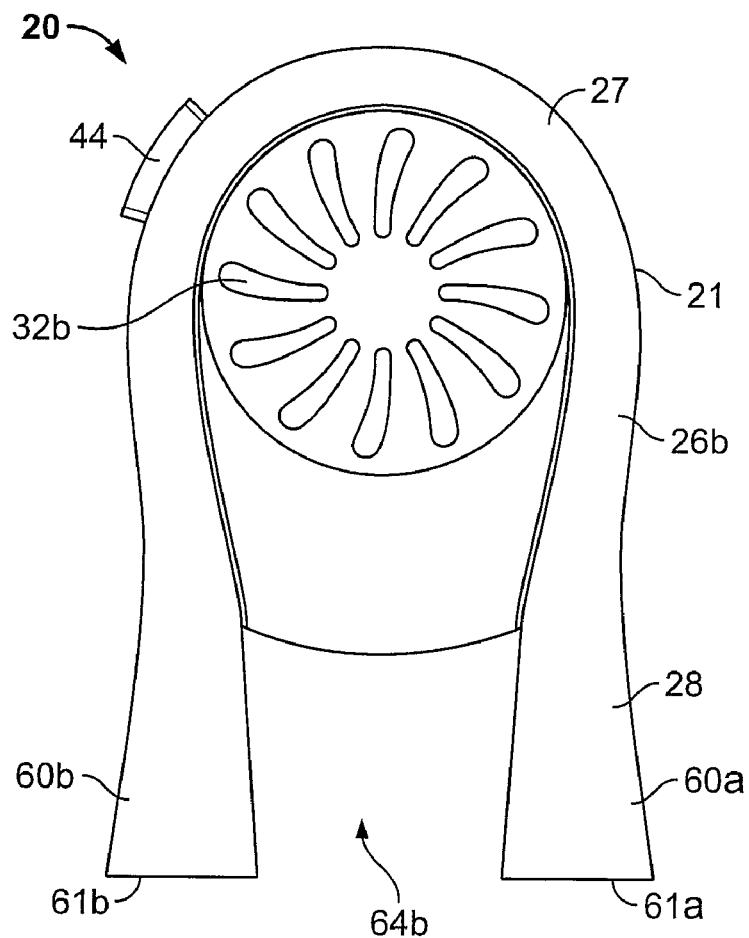
FIG. 4 is a an elevational view of a third side of the dispensing device of FIG. 1.
Figure 5:
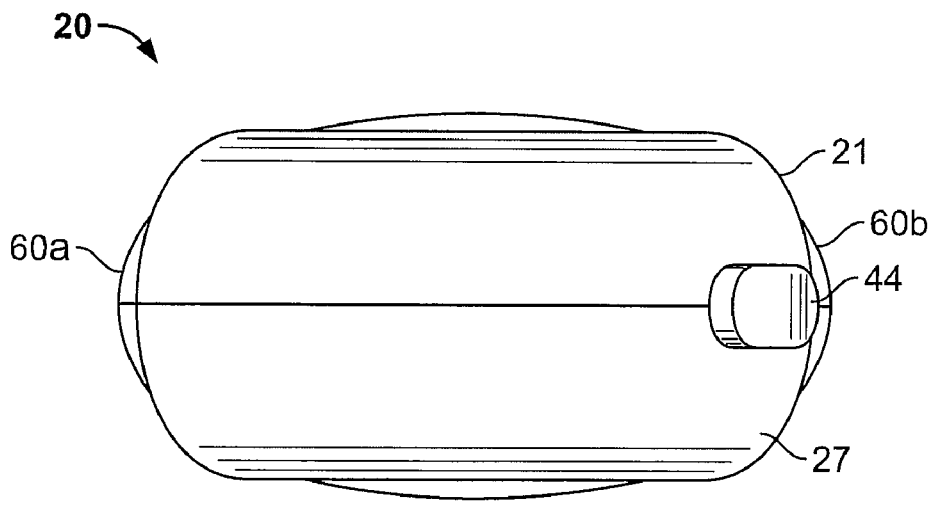
FIG. 5 is a plan view of the dispensing device of FIG. 1.
Figure 6A:
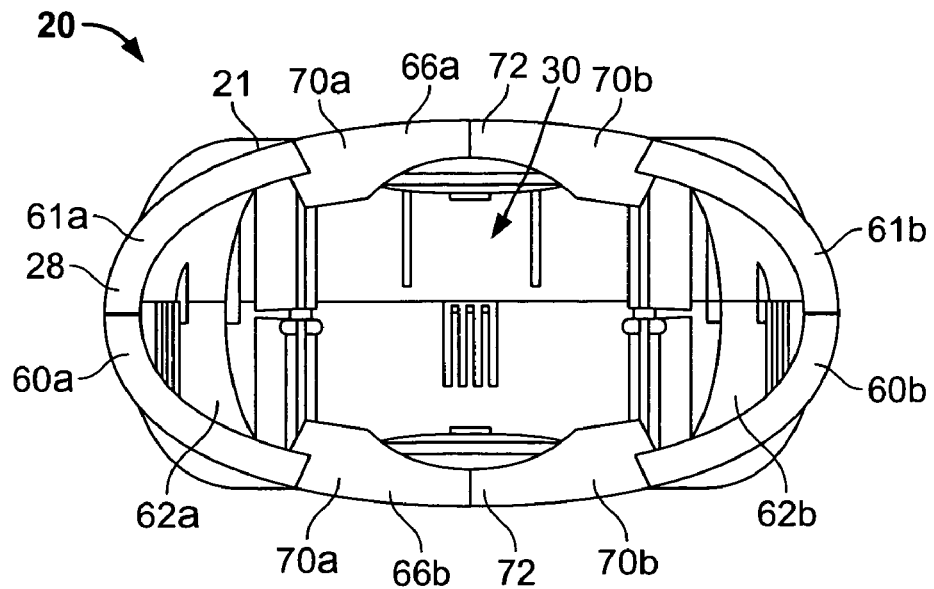
FIG. 6A is a bottom elevational view of the dispensing device of FIG. 1.
Figure 10:
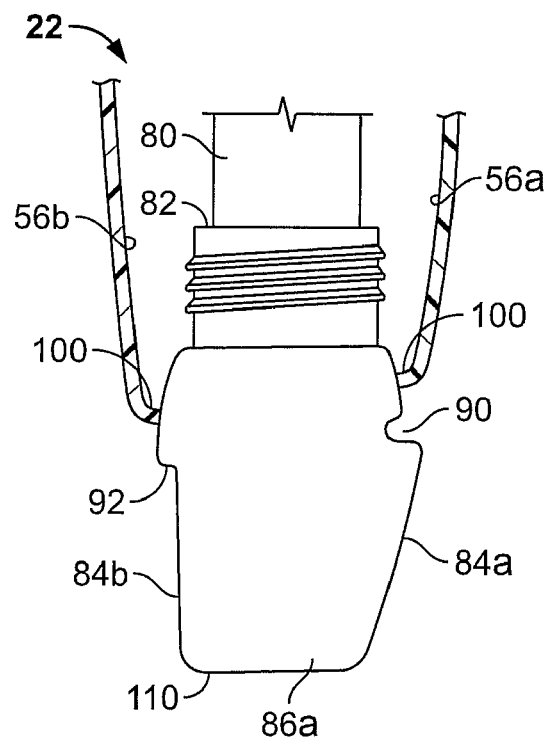
FIG. 10 is a partial cross-sectional, side elevational view of the container of FIG. 8 as it is inserted into the dispensing device of FIG. 1.
Figure 11:
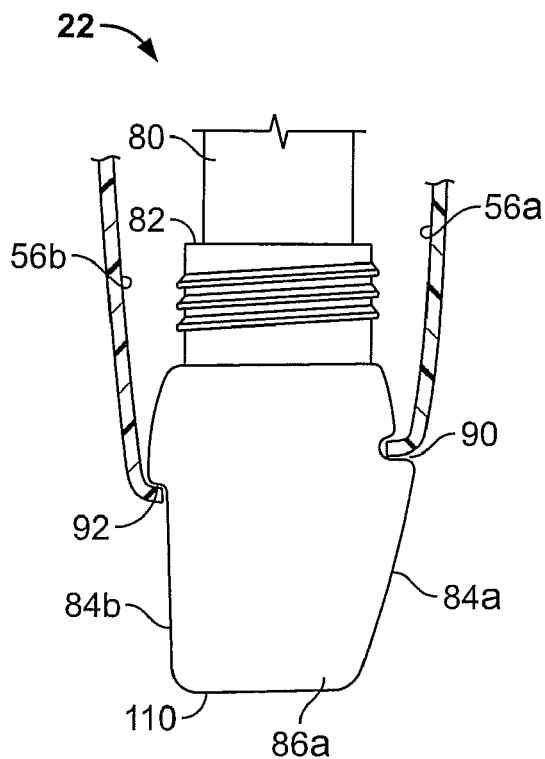
FIG. 11 is a partial cross-sectional, side elevational view of the container of FIG. 8 inserted in the disposing device of FIG. 1.

The lower housing portion 28 includes first and second spaced apart C-shaped legs 60a, 60b extending downwardly from the upper housing portion 27, wherein the legs 60a, 60b each include bottom surfaces 61a, 61b adapted to support the device 20 on a support surface 112. The first and second legs 60a, 60b form first and second inwardly facing cavities 62a, 62b, respectively that communicate with the interior cavity 30 of the upper housing portion 27. As seen in FIGS. 2 and 3, first and second opposed openings 64a, 64b are disposed in the first and second body portions 26a, 26b, respectively, of the lower housing portion 28 between the first and second legs 60a, 60b, wherein the first opening 64a has a height H1 that is greater than a height H2 of the second opening 64b. Referring to FIGS. 6, 10, and 11, first and second inwardly facing clips 66a, 66b extend inwardly from the inner surfaces 56a, 56b of the first and second body portions 26a, 26b, respectively, adjacent the first and second openings 64a, 64b. Each clip includes two outer engaging portions 70a, 70b surrounding a central indentation 72.

Figure 9:
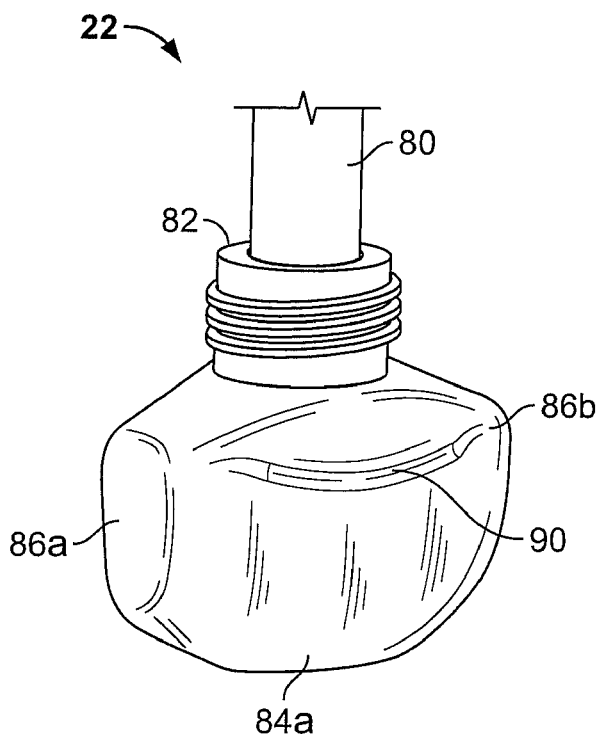
FIG. 9 is a front isometric view of a container for holding a liquid volatile material.

The container 22 for insertion into the passive dispensing device 20 is depicted in FIGS. 9-11. The container 22 includes a liquid active material (not shown) therein and a wick 80 in contact with the liquid active and extending out of the container 22 through a container opening 82. The container 22 is formed by first and second opposing longitudinal sidewalls 84a, 84b having a concave curvature and first and second opposing lateral sidewalls 86a, 86b connecting the longitudinal sidewalls 84a, 84b. A recess 90 is disposed in the first longitudinal sidewall 84a and a downwardly facing ledge 92 is formed in the second longitudinal sidewall 84b of the container 22. The recess 90 is disposed higher in the sidewall 84a than ledge 92 is disposed in the sidewall 84a, such that the recess 90 is closer to the opening 82 than the ledge 92.

Figure 6B:
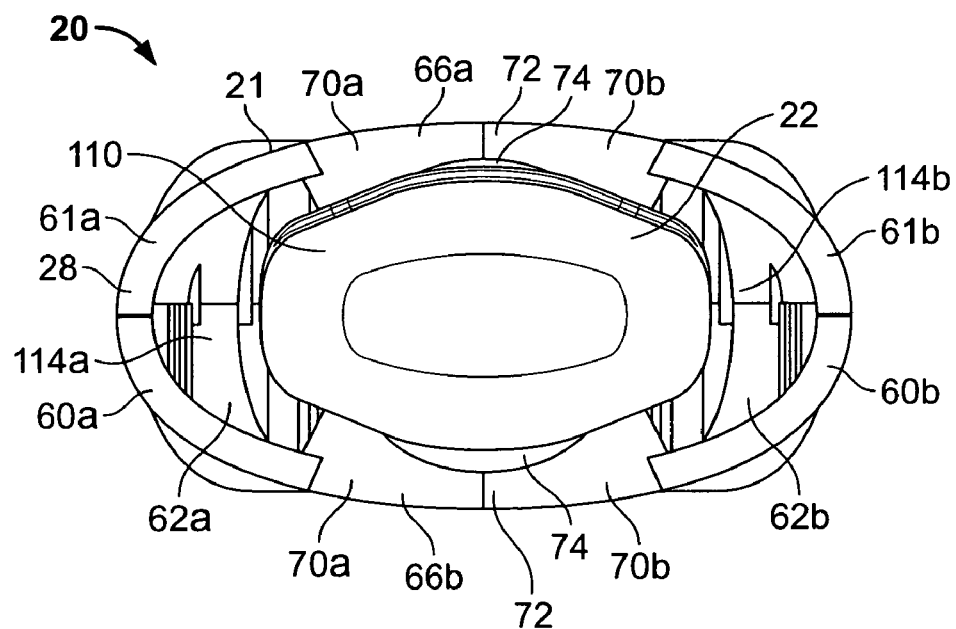
FIG. 6B is a bottom elevational view of the dispensing device of FIG. 1 having a container inserted therein.

The container 22 is releasably secured to the dispensing device 20 by inserting the wick 80 of the container 22 into the interior cavity 30 of the upper housing portion 27, inserting the container 22 into the first and second inwardly facing cavities 62a, 62b, and pushing the container 22 upwardly into the dispensing device 20. As seen in FIGS. 6B, 10, and 11, the outer engaging portions 70a, 70b of the first clip 66a engage walls defining the recess 90 in the first longitudinal sidewall 84a of the container 22 and an upper surface 100 of the outer engaging portions 70a, 70b of the second clip 66b engages the ledge 92 in the second longitudinal sidewall 84b of the container 22 to retain the container 22 within the dispensing device 20. The central indentations 72 provide passageways 74 between the container 22 and the respective clips 66a, 66b to allow movement of air through the passageways 74. A bottom surface 110 of the container 22 is spaced from the support surface 112 and first and second gaps 114a, 114b are formed between the container 22 and the first and second legs 60a, 60b to allow air to naturally flow upwardly under the container 22, through the first and second gaps 114a, 114b, into the interior cavity 30, and out the first and second sets of vents 32a, 32b if the vents 32a, 32b, are in an open position. The container 22 is removed from the dispensing device 20 by pulling the container 22 away from the interior cavity 30 of the upper housing portion 27. As the container 22 is pulled, the wall defining the recess 90 and the ledge 92 with the first and second clips 66a, 66b causes the first and second clips 66a, 66b and first and second body portions 26a, 26b of the upper housing portion 27 adjacent the clips 66a, 66b to flex outwardly, thereby allowing removal the container 22.

For manufacturing purposes, the first and second body portions 26a, 26b are formed as separate pieces and attached to one another during the manufacturing process. In particular, the first body portion 26a includes two posts 130a, 130b extending from respective supports 132a, 132b and the second body portion 26b includes two supports 134a, 134b having apertures 136a, 136b formed in the supports 134a, 134b. The posts 130a, 130b engage walls defining the apertures 136a, 136b to secure the first and second body portions 26a, 26b together. Other securement means may be used to attach the first and second body portions 26a, 26b in addition to or in place of the posts 130a, 130b and apertures 136a, 136b. For example, an adhesive may be used or an interference fit may be created between the first and second body portions 26a, 26b. Preferably, the dispensing device 20 is manufactured of a plastic material, such as polypropylene.

Although the body portions 26a, 26b are depicted as two pieces, the body portions 26a, 26b may alternatively be formed integrally with one another.

The dispensing device 20 may be provided to a consumer in a kit. For example, the dispensing device 20 may be packaged with a container 22 holding a liquid active material. Optionally, the dispensing device 20 may also be provided with a set of instructions regarding how to use the dispensing device 20 and/or container 22.

INDUSTRIAL APPLICABILITY

The present invention provides a passive active material dispensing device with greater dispersion of an active material therefrom by allowing air flow through the dispensing device. The dispensing device may be utilized inside a user's home for dispersion of a fragrance, odor eliminator, or the like or may be utilized outdoors for dispersion of an insect repellent, insecticide, or the like.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. All patents and other references cited herein are incorporated by reference in their entirety. The exclusive rights to all modifications which come within the scope of the appended claims are reserved.

We claim:

1. A passive dispensing device for a liquid active material, the dispensing device comprising:
    an upper housing portion for receiving a container for holding and dispensing a liquid active material, wherein the upper housing portion includes an interior cavity and wherein the container includes a wick extending from inside the container to an area outside the container;
    a lower housing portion that extends downwardly from the upper housing portion, wherein the lower housing portion defines a recess between the upper and lower housing portions and includes first and second legs that extend downwardly from the upper housing portion and outwardly from the recess;
    a first set of vents disposed in a first body portion of the upper housing portion;
    a second set of vents disposed in a second body portion of the upper housing portion; and
    a louver for opening and closing the first and second sets of vents,
    wherein the dispensing device has an operative position in which the first and second legs are disposed on a support surface, the container is retained in the recess with the wick extending upwardly into the interior cavity, and the container is spaced above the support surface and disposed between the first and second legs to allow convective air flow under the container, between the container and the first and second legs past the recess and the container, and through the device to dispense the active material from the upper housing.

2. The dispensing device of claim 1, wherein the first and second legs include first and second C-shaped walls, respectively, forming first and second cavities, respectively.

3. The dispensing device of claim 2, wherein the first and second cavities face inwardly toward one another.

4. The dispensing device of claim 3, wherein the first and second C-shaped walls and first and second cavities provide a guide for insertion of the container into the device.

5. The dispensing device of claim 4, wherein first and second gaps are formed between the container and the first and second C-shaped walls, respectively.

6. The dispensing device of claim 1, wherein first and second opposed openings are formed in first and second body portions between the first and second legs.

7. The dispensing device of claim 6, wherein first and second inwardly facing clips extend from opposing inner surfaces of the upper housing portion adjacent the first and second opposed openings, respectively.

8. The dispensing device of claim 7, wherein the first and second clips each include at least one engaging portion and an indentation.

9. The dispensing device of claim 8, wherein the engaging portion of the first clip engages walls defining a recess in a first wall of the container and the engaging portion of the second clip engages a ledge in a second wall of the container such that passageways are formed between the container and the indentations to allow air to flow into the upper housing portion.

10. A kit comprising:
    the passive dispensing device of claim 1;
    a container holding a liquid active material, and an optional set of instructions for a user.

11. A passive dispensing device for a liquid active material, the dispensing device comprising:
    a housing having first and second body portions defining upper and lower housing portions;
    first and second clips extending inwardly from the upper housing portion, wherein each of the clips includes two abutting outer engaging portions and an inner indentation therebetween;
    a container for holding the liquid active material, comprising:
        a wick extending from inside the container to an area outside the container;
        a recess disposed in a first wall of the container;
        a downwardly facing ledge disposed in a second wall of the container;
    wherein the container is disposed within the device such that the outer engaging portions of the first clip engage walls defining the recess, the outer engaging portions of the second clip engage the ledge, and the indentations form passageways between the container walls and the clips.

12. The dispensing device of claim 11, wherein a recess is defined between the upper and lower housing portions and the lower housing portion includes first and second legs extending downwardly from the upper housing portion and outwardly from the recess.

13. The dispensing device of claim 11, further including a set of vents disposed in a body portion of the upper housing portion and a louver for opening and closing the set of vents.

14. The dispensing device of claim 13, further including a second set of vents disposed in a second body portion of the upper housing portion and wherein the louver further opens and closes the second set of vents.

15. The dispensing device of claim 12, wherein the wick extends into a cavity formed by the upper housing portion and wherein the wick is disposed adjacent one or more vents.

16. A passive dispensing device for a liquid active material, the dispensing device comprising:
   a container for holding the liquid active material, wherein the container includes a wick extending from inside the container to an area outside the container;
   an upper housing portion for dispensing the active material, wherein the upper housing portion includes an interior cavity;
   a lower housing portion that extends downwardly from the upper housing portion, wherein the lower housing portion defines a recess between the upper and lower housing portions and the lower housing portion further includes first and second legs extending downwardly from the upper housing portion and outwardly from the recess; and
   first and second opposed openings formed between the first and second legs and first and second inwardly facing clips extending from opposing inner surfaces of the upper housing portion adjacent the first and second openings, respectively, wherein each of the first and second clips includes at least one engaging portion and an indentation, and further wherein the first and second clips engage the container such that passageways are formed between the container and the indentations to allow air to flow into the upper housing portion,
   wherein the dispensing device has an operative position in which the container is retained in the recess with the wick extending upwardly into the interior cavity, a bottom surface of the container is disposed above bottom surfaces of the legs, and the container is disposed between the first and second legs such that gaps are formed between the container and the legs to allow convective air flow under the container, through the gaps and the passageways past the container, and through the device to dispense the liquid active material from the upper housing.

17. The dispensing device of claim 16, wherein the engaging portion of the first clip engages walls defining a recess in a first wall of the container and the engaging portion of the second clip engages a ledge in a second wall of the container.

18. The passive dispensing device of claim 1, wherein the louver includes a first louver for opening and closing the first set of vents and a second louver for opening and closing the second set of vents.

19. The passive dispensing device of claim 1, wherein the louver is centered within the first and second sets of vents.

20. The dispensing device of claim 16, wherein each of the first and second clips includes two abutting outer engaging portions and the indentation is disposed therebetween.

* * * * *